United States Patent [19]

Arsac et al.

[11] 4,109,093

[45] Aug. 22, 1978

[54] PROCESS FOR MAKING 2-(4'-AMINOPHENYL) 5-AMINO BENZIMIDAZOLE

[75] Inventors: Aimé Joseph Arsac, Condrieu; Pierre Frank, Saint-Clair-Du-Rhone, both of France

[73] Assignee: Produits Chimiques Ugine Kuhlmann, Paris, France

[21] Appl. No.: 647,240

[22] Filed: Jan. 7, 1976

[30] Foreign Application Priority Data

Jan. 14, 1975 [FR] France ................................ 75 00924
Nov. 18, 1975 [FR] France ................................ 75 35129

[51] Int. Cl.² ............................................ C07D 235/18
[52] U.S. Cl. .................................................... 548/334
[58] Field of Search ........................ 260/309.2; 548/334

[56] References Cited

U.S. PATENT DOCUMENTS

| 3,013,051 | 12/1961 | Richter | 260/544 N |
|---|---|---|---|
| 3,095,422 | 6/1963 | Duennenberger et al. | 260/309.2 |
| 3,161,678 | 12/1964 | Thominet | 260/544 N |
| 3,192,226 | 6/1965 | Sarett et al. | 260/309.2 |
| 3,235,559 | 2/1966 | Blocher et al. | 260/309.2 |
| 3,466,330 | 9/1969 | Tanida et al. | 260/309.2 |
| 3,485,865 | 12/1969 | Richter et al. | 260/544 N |
| 3,586,694 | 6/1971 | Shen et al. | 260/309.2 |
| 3,632,397 | 1/1972 | Soper | 260/309.2 |
| 3,681,376 | 8/1972 | Scherer et al. | 260/309.2 |
| 3,822,311 | 7/1974 | Wedemeyer et al. | 260/544 N |

FOREIGN PATENT DOCUMENTS

70,862  7/1893  Fed. Rep. of Germany ........ 260/309.2

OTHER PUBLICATIONS

Kym Berichte 1899, vol. 32, pp. 2178–2180.
Porai-Koshits, Chem. Abst. 1958, vol. 52, columns 17240–17241.
Noller Chemistry of Organic Compounds, 2nd ed., pp. 160 & 244, Philadelphia, Saunders, 1957.

*Primary Examiner*—Natalie Trousof
*Attorney, Agent, or Firm*—Beveridge, Degrandi, Kline & Lunsford

[57] ABSTRACT

A process for preparing 2-(4'-aminophenyl) 5-amino benzimidazole, a known intermediate used in the synthesis of azo dyes, is disclosed wherein p-nitrobenzoic acid is condensed with aniline, and the N(4'-nitrobenzoyl) aniline produced is dinitrited to N(4'-nitrobenzoyl) 2,4-dinitroaniline; the latter is reduced to the corresponding triamine, which, upon cyclodehydration, results in the 2-(4'-aminophenyl) 5-amino benzimidazole.

2 Claims, No Drawings

PROCESS FOR MAKING 2-(4'-AMINOPHENYL) 5-AMINO BENZIMIDAZOLE

The present invention relates to a new process for the preparation of 2-(4'-amino-phenyl)-5-amino-benzimidazole.

This product described in column 17,240 g-h of the 52nd volume of Chemical Abstracts published in 1958, is normally prepared according to the following stages:
- condensation of p-nitrobenzoic acid chloride with 2,4-dinitroaniline in the absence of solvent, and
- reduction of the N-(4-nitrobenzoyl)-2,4-dinitro-aniline thus obtained with stannous chloride in the presence of concentrated hydrochloric acid.

This process has a number of disadvantages: (1) the condensation of the p-nitrobenzoic acid chloride with 2,4-dinitro-aniline liberates hydrochloric acid. It follows that the operation has to be conducted in a special apparatus which is resistant to corrosion by concentrated hydrochloric acid. (2) the 2,4-dinitro-aniline is a difficultly obtainable product and therefore expensive. (3) the stannous chloride is not a common industrial product. (4) The reduction in the presence of concentrated hydrochoric acid necessitates an apparatus resistant to corrosion.

It has now been found that it is possible to prepare 2-(4'-amino-phenyl)-5-amino-benzimidazole in a simple manner and without the use of expensive substances or special material, under particularly advantageous economic conditions and with excellent yields.

According to the invention, a process for the preparation of 2-(4'-amino-phenyl)-5-amino-benzimidazole (hereinafter referred to as DAPBI) is provided which comprises carrying out successively the condensation of p-nitro-benzoic acid with aniline, the dinitration of the N-(4'-nitro-benzoyl)aniline obtained, the reduction of the resulting N-(4-nitro-benzoyl)-2,4-dinitro-aniline to the corresponding triamine, and then dehydrocyclisation of the triamine leading to the DAPBI.

The condensation is preferably effected at a temperature about 170° C., the water formed during the reaction being distilled off.

The dinitration is effected more especially at a temperature between 0° C. and 25° C. in the presence of concentrated sulphuric acid and concentrated nitric acid.

According to a preferred form of the invention, the N-(4'-nitrobenzoyl)-2,4-dinitroaniline is prepared by treating the p-nitrobenzoic acid with a chlorinating agent so as to form the acid chloride, carrying out the condensation of this chloride with aniline leading to the N-(4'-nitro-benzoyl)-aniline, then reacting the latter with nitric acid to obtain the trinitroderivative in a single manufacturing cycle, that is, without isolating the acid chloride or the N-(4'-nitrobenzoyl)-aniline formed intermediately.

According to the invention, it is advantageous to use stoichiometric proportions of p-nitrobenzoic acid, aniline and then of nitric acid.

We have also found that a much purer N-(4'-nitrobenzoyl)-2,4-dinitroaniline is obtained by working in an aliphatic solvent medium. In addition, since the new process does not require very high reaction temperatures, it is less costly.

According to the new process, the 4-nitrobenzoic acid chloride is condensed with aniline and the 4-nitrobenzanilide formed is extracted and nitrated.

The halide of the 4-nitrobenzoic acid is directly prepared by reacting a halogenating agent with 4-nitrobenzoic acid. The halogenating agent may be for example phosphorus pentachloride, or phosphorus pentabromide, but is preferably thionyl chloride. The reaction is effected in an inert aromatic or, preferably, aliphatic solvent such as, for example, 1,2-dichloroethane or 1,1,2,2-tetrachloroethylene. The operation may be effected in the presence of a small quantity of dimethyl formamide which favours the formation of the acid chloride and is advantageously carried out at the reflux temperature of the solvent.

The condensation with aniline is advantageously effected in the same solvent. Since the reaction is very rapid, it is favourable to add the aniline cautiously to the 4-nitrobenzoic acid chloride previously formed.

For the nitration of the N-(4'-nitrobenzoyl)-aniline formed, the solvent may be removed by filtration or by distillation in steam, but is more advantageous to avoid the many handling operations which these operations entail.

The applicant has in fact found that it is possible to separate the N-(4'-nitrobenzoyl-aniline) form the medium in which it is formed by extraction with sulphuric acid. It is then sufficient to react the solution obtained with nitric acid to obtain a N-(4'-nitrobenzoyl)-2,4-dinitro-aniline of great purity and with a practically quantitative yield.

According to the invention, it is advantageous to effect the reduction of the N-(4'-nitrobenzoyl)-2,4-dinitro-aniline by means of sodium of ammonium hydrosulphide, or sodium or ammonium sulphide or polysulphide or the mixed sulphides or polysulphides of sodium and ammonium.

The DAPBI may be isolated for example in alkaline medium, preferably at a pH between 7 and 10, after the dehydrocyclisation, and the operation may be carried out in an ammoniacal medium or in a sodium carbonate or caustic soda medium.

The DAPBI may also be isolated for example in acid medium in the form of the monohydrochloride after the dehydrocyclisation.

According to an advantageous form of the invention, the reduction and the dehydrocyclisation are effected without intermediate isolation of the triamine. This results in a considerable reduction of the cost of manufacture.

According to the invention, the designation DAPBI includes not only 2-(4'-amino-phenyl)-5-amino-benzimidazole, but also, although subsidiarily, its 6-chloro and 6-alkyl derivatives.

As we have show, the DAPBI prepared by the process of the invention constitutes a valuable intermediate material for the synthesis of azo dyestuffs.

The invention is illustrated by the following Examples, in which the parts are parts by weight.

EXAMPLE 1 Preparation of N-(4'-nitrobenzoyl)-aniline

A mixture of 167 parts of p-nitrobenzoic acid and 93 parts of aniline is heated at 210° C. with the water formed during the reaction being distilled off. After heating for 3 hours, 18 parts of water have been collected, which shows that the reaction is ended. 242 parts of N-(4'-nitrobenzoyl)-aniline melting at 215° C. are obtained according to the instructions in the literature, i.e. a yield of 99% by weight. The infra-red spectrum confirms the formula of the product:

band at 1660 cm$^{-1}$ characteristic of the amidefunction, band at 1320 cm$^{-1}$ and 1350 cm$^{-1}$ characteristic of the nitro group.

The purity of the product is from 98 to 99% checked by gas-liquid chromatography.

If the operation is carried out for 6 hours at 175° C. or 4 hours at 195° C, just as good a product is obtained, with a quantitative yield.

EXAMPLE 2 Preparation of N-(4'-nitrobenzoyl)-2,4-dinitroaniline 242 parts of N-(4'-nitrobenzoyl)-aniline are dissolved in 2000 parts of 66° Be sulphuric acid, then the solution is cooled to 0° C. Then a solution of 130 parts of nitric acid in 70 parts of 66° Be sulphuric acid is added in a period of 2 hours. The mixture is allowed to react for 1 hour at 10° C. then for 2 hours at 25° C., and this solution is then added slowly to 2000 parts of water and 3000 parts of ice. The product obtained is filtered off and washed with water to remove excess acid, and then dried. 329 parts of a product melting at 195° C. are obtained conforming to the information in the literature, and the yield is 90% by weight.

If instead of 2000 parts of sulphuric acid, 1000 parts of the same acid are used, the same product with the same yield is obtained.

EXAMPLE 3

860 parts of tetrachloroethylene, 167 parts of p-nitrobenzoic acid and 5 parts of dimethyl formamide are placed in a reactor and the mixture is heated at 80° C. and 120 parts of thionyl chloride are added in a period of an hour while a gentle reflux is maintained. The refluxing is maintained until the end of the reaction, which is verified by the fact that the reflux temperature then reaches 121° C.

The product is then cooled to 80° C. and 93 parts of aniline are added in a period of 30 minutes. On account of the reaction being exothermic, the temperature reaches 100° C. at the end of the addition. The mixture is then brought to the refluxing temperature, maintained at this for 30 minutes, and then cooled to 20° C.

then 450 parts of 94.2% sulphuric acid and 100 parts of oleum containing 20% of free SO$_3$ are added. The mixture is stirred for an hour until all the N-(4'-nitrobenzoyl)-aniline has dissolved, then the acid solution is separated from the solvent by decantation.

Then a further 500 parts of oleum containing 20% of SO$_3$ are added to the acid solution and then the solution of 126 parts of nitric acid in 60 parts of 100% sulphuric acid is added in a period of 4 hours at a temperature between 15° C. and 25° C. It is allowed to react for a further 30 minutes, then hydrolysed by means of 2000 parts of water and 3000 parts of crushed ice. The product is precipitated and is isolated by filtration followed by washing with water in order to eliminate excess acid, and drying. 329 parts of the trinitro derivative melting at 196° C. are obtained, the yield being 99% by weight. On operating in 1,2-dichloroethane or 1,1,2-trichloroethylene, a product of identical quality is obtained.

A sulphuric acid containing less water may be used; in this case, an oleum containing less free SO$_3$ is used.

It is possible to work in the absence of dimethyl formamide, and the same product is obtained, but the formation of the acid chloride takes an hour longer.

EXAMPLE 4: Preparation of N$_1$-(4'-aminobenzoyl)-1,2,4-triaminobenzene

A mixture of 332 parts of N-(4'-nitrobenzoyl)-2,4-dinitroaniline and 2000 parts of water is heated to 80° C, then a solution of 300 parts of sodium hydrosulphide in 600 parts of water is added in a period of an hour. The temperature rises to 100° C. The solution is refluxed for 2 hours and then cooled to 20° C. filtered, and the product washed with water and dried. About 200 parts of a triamino product melting at 204°–205° C. are obtained.

If the sodium hydrosulphide is replaced by 330 parts of sodium disulphide or by 550 parts of sodim tetrasulphide, or by 360 parts of a mixture of sodium and ammonium sulphides, the same product is obtained.

EXAMPLE 5: Preparation of the DAPBI 242 parts of N$_1$-(4'-aminobenzoyl)-1,2,4-triamino-benzene are dissolved in 500 parts of a 20° Be solution of hydrochloric acid and 1000 parts of water, and the mixture is then heated at 100° C. for 3 hours. 1000 parts of ice and then 500 parts of a 20° Be solution of ammonia are added. The precipitate is filtered off and dried. 210 parts of 2-(4'-amino-phenyl)-5-aminobenzimidazole are thus obtained.

After recrystallisation from ethanol, then heating at 170° C for an hour, the product melts at 235° C., conforming to the information in the literature.

Analysis C$_{13}$H$_{12}$N$_4$ Molecular weight 224.26 Calculated: C, 69.62%; H, 5,40%; N, 24.98%. Found: C, 68.85%; H, 5.48%; N, 24.75%.

Infra-red spectrum in KBr

The presence of the following characteristic bands is found:

bands at 3350 cm$^{-1}$, 1410 cm$^{-1}$ and 1380 cm$^{-1}$ characteristic of the linkage C-NHband at 1620 cm$^{-1}$ characteristic of the linkage C = N - bands at 960 cm$^{-1}$ and 840 cm$^{-1}$ characteristic of the 1,2,4-benzene substitutions, band at 810 cm$^{-1}$ characteristic of the 1,4-benzene substitutions.

EXAMPLE 6

The trinitro derivative is reduced according to the instructions in Example 4 but instead of cooling the solution obtained, 750 parts of a 20° Be solution of hydrochloric acid are added and the mixture is heated for a further 3 hours at 100° C. The product is cooled to 20° C. the traces of precipitate are removed by filtration, and then a 20° Be solution of ammonia is added so as to obtain pH 8. The precipitate is filtered off and dried. 200 parts of the same product as in Example 5 are obtained.

If the ammonia solution is replaced by a 36° Be solution of caustic soda or a 20% sodium carbonate solution, the same produce is obtained.

EXAMPLE 7

600 parts of a 10N solution of ammonia, then 380 parts of sodium hydrosulphide are successively added to 2000 parts of water. The mixture is heated to 90° C., and 332 parts of N-(4'-nitrobenzoyl)-2,4-dinitro-aniline are introduced in a period of 2 hours. The mixture is brought to reflux and maintained under reflux for 2 hours, cooled to 90° C., 2000 parts of a 20° Be solution of hydrochloric acid are added and the mixture is again refluxed and agitated for 2 hours. It is filtered to eliminate traces of sulphur and the filtrate is made alkaline by a 36° Be solution of caustic soda to pH 8. The precipitate obtained is filtered off and dried. 200 parts of the same product as in Example 4 are obtained. The yield of DAPBI with respect to the N-(4'-nitrobenzoyl)-2,4-dinitro aniline used was 89% by weight.

If the caustic soda is replaced by an equivalent amount of ammonia or sodium carbonate, the same product is obtained.

If after 2 hours refluxing in an acid medium, an amount of salt is added such that a 20% solution of sodium chloride is obtained, say about 1000 parts, and that after having cooled to 10° C, a 36° Be solution of caustic soda is added to bring the solution to pH 2, 245 parts of the monohydrochloride of DAPBI are obtained, which corresponds to a chemical yield of 94%.

If 800 parts of hydrochloric acid are used instead of 2000 parts, after 2 hours heating the monohydrochloride of 2-(4'-amino-phenyl)-5-amino-benzimidazole is obtained, which is filtered off without making the solution alkaline.

What we claim is:

1. A process for the preparation of 2-(4'-amino phenyl)-5-amino benzimidazole (DAPBI) wherein p.nitrobenzoic acid is condensed with aniline to obtain N-(4'nitrobenzoyl)-aniline, the N-(4'-nitrobenzoyl)-aniline is dinitrated at a temperature of between 0° and 25° C. in the presence of concentrated sulphuric acid and concentrated nitric acid to obtain N-(4'-nitrobenzoyl)-2,4-dinitroaniline, the N-(4'-nitrobenzoyl)-2,4-dinitroaniline is reduced to the corresponding triamine, and the deshydrocyclization of the triamine is carried out to obtain the DAPBI, wherein the improvement consists essentially of: treating p.nitrobenzoic acid with a halogenating agent in an inert aliphatic solvent medium to form the acid halide, and carrying out the condensation of the acid halide with aniline in the said inert aliphatic solvent medium with stoichiometric proportions of p.nitrobenzoic acid and aniline without isolating the acid halide; extracting the N-(4'-nitrobenzoyl)-aniline from the solvent medium with sulphuric acid and dinitrating it in its sulphuric acid solution with stoichiometric proportion of nitric acid without intermediate isolation of the N-(4'-nitrobenzoyl)aniline.

2. A process for the preparation of 2-(4'-amino phenyl)-5-amino benzimidazole (DAPBI) wherein p.nitrobenzoic acid is condensed with aniline to obtain N-(4'-nirobenzoyl)-aniline, the N-(4'-nitrobenzoyl)-aniline is dinitrated at a temperature of between 0° and 25° C. in the presence of concentrated sulphuric acid and concentrated nitric acid to obtain N(4'-nitrobenzoyl)-2,4-dinitroaniline, the N-(4'-nitrobenzoyl)-2,4-dinitroaniline is reduced to the corresponding triamine, and the deshydrocyclization of the triamine is carried out to obtain the DAPBI, wherein the improvement consists essentially of: treating p.nitrobenzoic acid with a halogenating agent in an inert aliphatic solvent medium to form the acid halide, and carrying out the condensation of the acid halide with aniline in the said inert aliphatic solvent medium with stoichiometric proportions of p.nitrobenzoic acid and aniline without isolating the acid halide; extracting the N-(4'-nitrobenzoyl)-aniline from the solvent medium with sulphuric acid and dinitrating it in its sulphuric acid solution with stoichiometric proportion of nitric acid without intermediate isolation of the N-(4'-nitrobenzoyl)aniline; reducing the N-(4'-nitrobenzoyl)-2,4-dinitroaniline by means of sodium or ammonium hydrosulphide or sodium or ammonium sulphide or polysulphide or mixed sulphide or polysulphide of sodium or ammonium, and effecting the reduction and the dehydrocyclization without intermediate isolation of the triamine.

* * * * *